US00PP24946P3

(12) United States Plant Patent
White

(10) Patent No.: US PP24,946 P3
(45) Date of Patent: Oct. 7, 2014

(54) APPLE TREE NAMED 'PREMA96'

(50) Latin Name: ***Mallus domestica* Mill**
Varietal Denomination: PremA96

(75) Inventor: Allan White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 13/441,751

(22) Filed: Apr. 6, 2012

(65) Prior Publication Data

US 2013/0074225 P1 Mar. 21, 2013

Related U.S. Application Data

(60) Provisional application No. 61/517,139, filed on Apr. 13, 2011.

(51) Int. Cl.
*A01H 5/00* (2006.01)
*A01H 5/08* (2006.01)

(52) U.S. Cl.
CPC ..... *A01H 5/0875* (2013.01)
USPC ..... Plt./161; Plt./156

(58) Field of Classification Search
USPC ..... Plt./156, 161
See application file for complete search history.

(56) References Cited

PUBLICATIONS

'Prevar' http://www.freshplaza.com/news_detail.asp?id+64128) retrieved from the internet on Aug. 19, 2013. (1 page total).*

* cited by examiner

*Primary Examiner* — Susan McCormick Ewoldt
(74) *Attorney, Agent, or Firm* — Ballew Law

(57) ABSTRACT

A new and distinct apple tree named 'PremA96' is disclosed. The new apple is notable for its attractive appearance, superb texture, improved flavor and long shelf life.

2 Drawing Sheets

Latin name of the genus and species of the plant claimed: *Mallus domestica* Mill.

Variety denomination: 'PREMA96'.

BRIEF DESCRIPTION OF THE PHOTOGRAPHS

Figure 1:
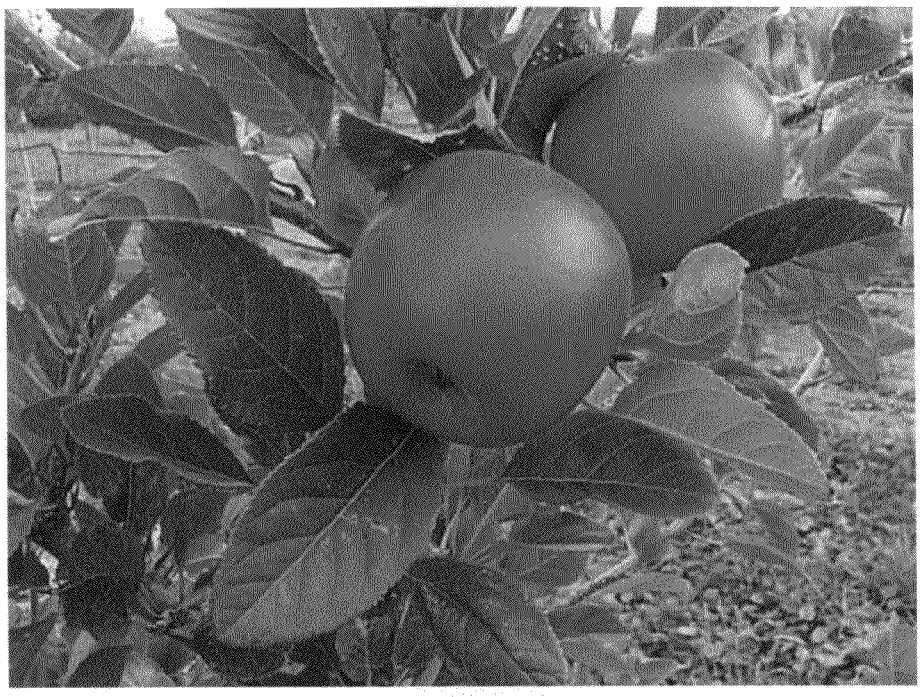
Figure 2:
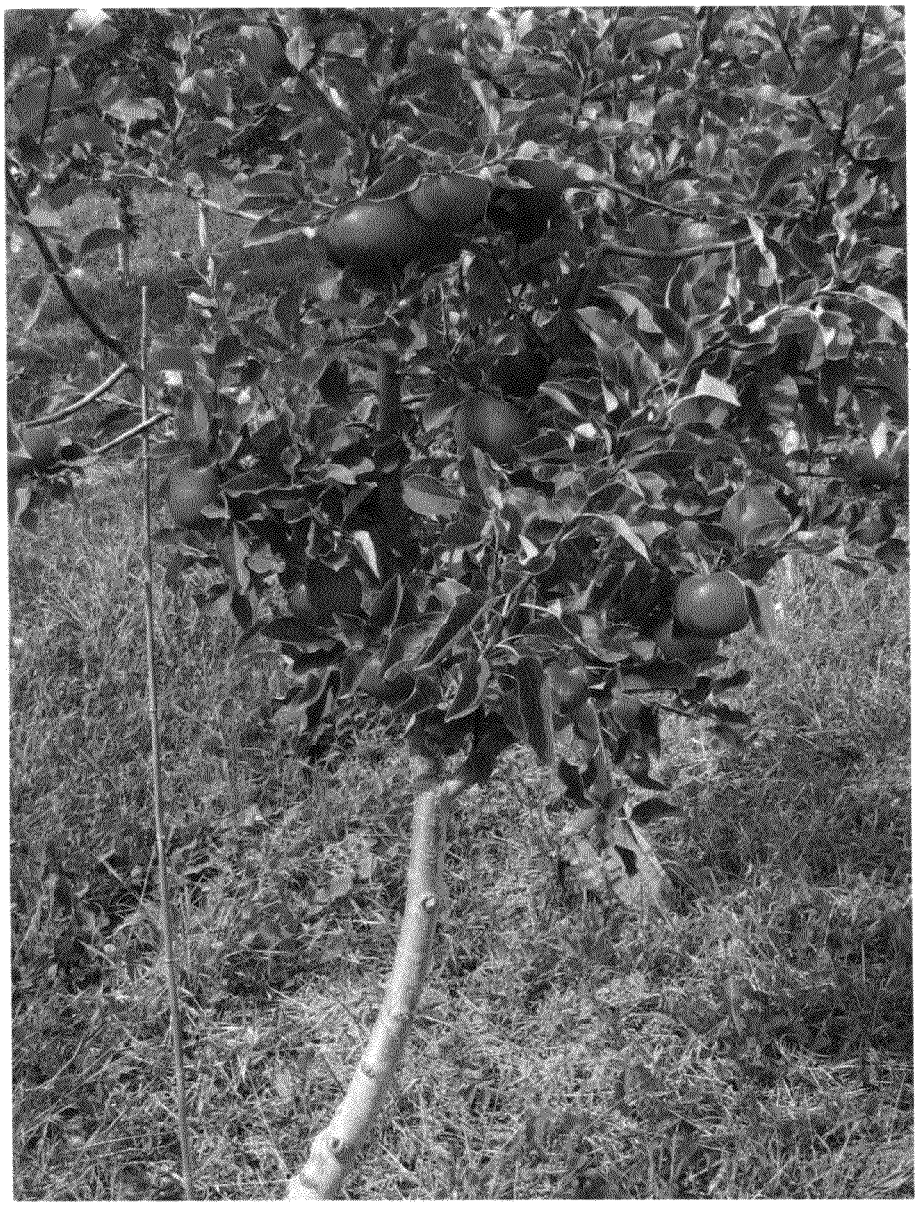

FIG. 1 shows the fruit of a 3 year old 'PremA96' apple tree;
FIG. 2 shows a 3 year old 'PremA96' apple tree;

BRIEF DESCRIPTION OF THE VARIETY

The new variety of apple tree 'PremA96' was created in the course of a planned breeding program carried out at The New Zealand Institute for Plant and Food Research, Hawkes Bay, New Zealand. 'PremA96' originated as a result of a controlled cross of 'Royal Gala' (U.S. Plant Pat. No. 4,121, patent expired) and 'GS 2184' (pollen parent, not patented). 'PremA96' was selected in 1996 as a single plant from among a population of seedlings derived from the parents, and was selected for its attractive red color and unique appearance, superb texture and flavor, and long shelf life. The fruit from 'PremA96' is smaller in size than both parent varieties, has more color than 'Royal Gala', and ripens earlier than 'GS 2184.' The fruit of 'PremA96' is smaller than 'Sweetie' (U.S. Plant Pat. No. 19,762). Asexual propagation by budding was first carried out in Nelson, New Zealand. The variety has since been observed over a number of asexually propagated generations, and has been found to remain true to type.

DETAILED BOTANICAL DESCRIPTION OF THE VARIETY

The following detailed botanical description is based on observations made during the 2011 growing season at Parker, Wash. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Age of observed variety.*—4 years.
- *Habit.*—Spreading.
- *Size.*—Height 219 cm, spread 143 cm.
- *Trunk.*—Diameter at 30 cm above graft union 4 cm.
- *Bark texture.*—Smooth.
- *Bark overcolor.*—198D.
- *Bark undercolor.*—166D.
- *Lenticels diameter.*—0.4 cm.
- *Lenticels color.*—155D.

Branch:
- *Size.*—Length 30.7 cm, Diameter 0.9 cm at 1 m above graft union.
- *Crotch angle relative to trunk.*—50°.
- *Branch color.*—165A.
- *Lenticel size.*—0.1 cm diameter.
- *Lenticel color.*—155D.
- *Lenticel density.*—13 per square inch.

Dormant one-year-old shoot:
- *Size.*—Length 43 cm, diameter 0.3 cm.
- *Color.*—165A.
- *Internode length.*—2.1 cm.
- *Lenticels.*—Quantity 24 per square inch, color 155D, diameter 0.1 cm.

Winter hardiness: Hardy for Washington State.
*Chilling requirement*.—Medium.
Leaf:
*Blade margin*.—Serrated.
*Size*.—Length 8.2 cm, width 4.9 cm.
*Color*.—Upper surface 143C.
*Color of lower surface*.—143D.
*Attitude in relation to shoot*.—50°.
Petiole:
*Length*.—1.6 cm.
*Diameter*.—0.2 cm.
*Color*.—63A.
Flower buds:
*Quantity per spur*.—5.
*Length*.—1 cm.
*Diameter*.—0.5 cm.
*Color*.—186B.
Flowers:
*Color at balloon stage*.—186B.
*Diameter of open flower*.—4 cm.
*Relative position of petal margin*.—Not touching.
*Depth*.—1.5 cm.
*Number per cluster*.—4 to 5.
Petals:
*Number per flower*.—5.
*Length*.—2 cm.
*Width at widest point*.—1.5 cm.
*Color of upper and lower surface*.—155C.
*Color of vein*.—186C.
*Margin*.—Not touching, smooth edges.
Pistils:
*Size*.—0.6 cm.
*Color*.—2B.
Anthers:
*Quantity*.—10.
*Size*.—0.2 cm.
*Color of pollen*.—2 B.
Stigma:
*Size*.—0.1 cm.
*Color*.—2C.
Style:
*Size*.—1.6 cm.
*Color*.—2C.
Ovary:
*Size*.—0.4 cm.
*Color*.—141D.
Bloom:
*Date of first bloom in Parker, Wash*.—April 30$^{th}$.
*Date of full bloom*.—May 5$^{th}$.
Pedicel:
*Length*.—2 cm.
*Diameter*.—0.1 cm.
*Color*.—175B.
Sepals:
*Quantity*.—5.
*Length*.—0.2 cm.
*Diameter*.—0.7 cm.
*Color*.—145A.
Fruit:
*Quantity per cluster*.—3-5.
*Size*.—Diameter 7 cm, length 6.6 cm; Average weight 100 g; General shape in profile globose.
*Aperture of eye*.—2 cm.
*Depth of eye basin*.—1 cm.
*Stalk*.—Diameter.—0.3 cm, length 3 cm; Depth of stalk cavity 0.5 cm; Width of stalk cavity 1 cm; Size of lenticels 0.1 cm.
*Ground color of skin*.—Yellow 3A.
*Over color of skin*.—Orange N25A to Red 47A.
*Amount of over color*.—90%.
*Intensity of over color*.—Medium.
*Pattern of over color*.—Blush.
*Flesh*.—Texture is fine and very juicy; Flesh color 11C.
*Quantity of seeds*.—9.
*Seed shape*.—Length 0.9 cm, Diameter 0.5 cm.
*Seed color*.—16A.
Productivity of fruit: 60,000 lbs per acre.
Harvest: 1$^{st}$ to 2$^{nd}$ week of September in Parker, Wash.
Storability: Can be stored at 32° for five months.
Plant disease resistance/susceptibility: None noted.
Pollination requirement: Any diploid that blooms at the same time.
Use: Fresh Market.

The invention claimed is:

1. I claim a new and distinct apple tree substantially as shown and described herein.

* * * * *